(12) United States Patent  
Dorn (10) Patent No.: US 10,945,696 B2
(45) Date of Patent: Mar. 16, 2021

(54) DETERMINING A REFERENCE DOSE PARAMETER OF A COMPUTED TOMOGRAPHY IMAGING

(71) Applicant: Siemens Healthcare GmbH, Erlangen (DE)

(72) Inventor: Karlheinz Dorn, Kalchreuth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 9 days.

(21) Appl. No.: 16/404,947

(22) Filed: May 7, 2019

(65) Prior Publication Data

US 2019/0254620 A1 Aug. 22, 2019

Related U.S. Application Data

(63) Continuation of application No. 15/939,377, filed on Mar. 29, 2018.

(30) Foreign Application Priority Data

Apr. 5, 2017 (EP) .................................. 17164992

(51) Int. Cl.
*A61B 6/03* (2006.01)
*A61B 6/00* (2006.01)

(52) U.S. Cl.
CPC ............ *A61B 6/5258* (2013.01); *A61B 6/032* (2013.01); *A61B 6/488* (2013.01); *A61B 6/52* (2013.01);

(Continued)

(58) Field of Classification Search
None
See application file for complete search history.

(56) References Cited

U.S. PATENT DOCUMENTS 7,031,423 B2 * 4/2006 Tsukagoshi ............ A61B 6/032
378/19
7,693,252 B2 * 4/2010 Noshi .................... A61B 6/465
378/4

(Continued)

FOREIGN PATENT DOCUMENTS

| CN | 106019352 A | 10/2016 |
|---|---|---|
| WO | WO-2013049818 A1 | 4/2013 |
| WO | WO-2013103790 A1 | 7/2013 |

OTHER PUBLICATIONS

Noferini, Linhsia et al. "Considerations on the practical application of the size-specific dose estimation (SSDE) method of AAPM Report 204" Radiological Physics and Technology, vol. 7, No. 2, pp. 296-302, Apr. 2014 // DOI: 10.1007/s12194-014-0265-2.

(Continued)

*Primary Examiner* — Thomas R Artman
(74) *Attorney, Agent, or Firm* — Harness, Dickey & Pierce, P.L.C.

(57) ABSTRACT

In a method, a topogram of an examination volume is received via an interface. A water equivalent diameter (abbreviated to WED) of a slice plane of the examination volume is then determined, via a computer unit, based on the topogram. Thereafter, via the computer unit, a noise level is determined based on the WED, the noise level being an upper threshold value for noise of a CT image dataset. Finally, via the computer unit, a reference dose parameter is determined, based on the noise level determined and the WED, the reference dose parameter corresponding to a first x ray dose, absorbable in the slice plane during a recording of a first CT image dataset of the examination volume upon noise of the first CT image dataset corresponding to the noise level determined.

20 Claims, 2 Drawing Sheets

(52) U.S. Cl.
CPC .............. *A61B 6/542* (2013.01); *A61B 6/544* (2013.01); *A61B 6/545* (2013.01)

(56) References Cited

U.S. PATENT DOCUMENTS

| | | | |
|---|---|---|---|
| 8,270,560 B2 | 9/2012 | Hirokawa et al. | |
| 9,592,022 B2 * | 3/2017 | Larson | A61B 6/463 |
| 9,877,695 B2 | 1/2018 | Lou et al. | |
| 10,105,110 B2 * | 10/2018 | Lou | A61B 6/482 |
| 2005/0008115 A1 * | 1/2005 | Tsukagoshi | A61B 6/463 |
| | | | 378/4 |
| 2006/0274877 A1 * | 12/2006 | Noshi | A61B 6/032 |
| | | | 378/4 |
| 2014/0270053 A1 * | 9/2014 | Larson | A61B 6/032 |
| | | | 378/4 |
| 2016/0063686 A1 | 3/2016 | Lou et al. | |
| 2016/0135777 A1 | 5/2016 | Lou et al. | |
| 2016/0183355 A1 * | 6/2016 | Lou | A61B 6/482 |
| | | | 378/112 |

OTHER PUBLICATIONS

Chinese Office Action and English translation thereof dated Apr. 25, 2019.

McCollough, Cynthia et al.: "The Measurement, Reporting, and Management of Radiation Dose in CT"; in: AAPM Report; vol. 96; ISBN: 978-1-888340-73-0; 2008.

McCollough, Cynthia et al.: "Use of Water Equivalent Diameter for Calculating Patient Size and Size-Specific Dose Estimates (SSDE) in CT"; in: AAPM Rep.; pp. 6-23; XP055446368; 2014.

Menke, Jan: "Comparison of Different Body Size Parameters for Individual Dose Adaptation in Body CT of Adults"; in: Radiology; vol. 236 No. 2; pp. 565-571; XP055075512; ISSN: 0033-8419; DOI:10.1148/radiol.2362041327; 2005.

European Search Report for European Application No. 17164992.4 Dated Oct. 20, 2017.

* cited by examiner

DETERMINING A REFERENCE DOSE PARAMETER OF A COMPUTED TOMOGRAPHY IMAGING

PRIORITY STATEMENT

The present application is a continuation of and hereby claims priority under 35 U.S.C. § 120/121 to pending U.S. patent application Ser. No. 15/939,377 filed Mar. 29, 2018, which claims priority to 35 U.S.C. § 119 to European patent application number EP17164992.4 filed Apr. 5, 2017, the entire contents of each of which are hereby incorporated herein by reference.

FIELD

At least one embodiment of the application is generally related to a method of determining a reference dose parameter of a computer tomography image; and/or parameter determination unit; and/or a computer readable storage medium.

BACKGROUND

The aim in computed tomography imaging, as well as obtaining a good image quality, is also that the respective examination volume absorbs an x-ray dose that is as small as possible, since a high x-ray dose can lead to potential damage to parts of the examination volume. This aim is also referred to as ALARA (an acronym for "as low as reasonably achievable").

In such cases, with an increasing x-ray dose, the noise in the resulting image dataset generally decreases, whereby the image quality increases. Computed tomography imaging can thus be referred to as optimum when the image quality is selected as just good enough, and thus when the x-ray dose is just high enough to still make a unique diagnosis of the resulting image possible. It is therefore usual to include dose parameters, for planning and/or for evaluating computed tomography imaging.

It is known that a dose parameter can be calculated in relation to an axial slice plane of the examination volume based on an axial slice image and further recording parameters, for example by way of a Monte-Carlo simulation. Here however the x-ray dose can only be calculated after the computed tomography imaging, thus the x-ray dose here is only a result of the computed tomography imaging. Furthermore, with this method, very many slice images must be transmitted and analyzed, if the x-ray dose is to be determined in a larger region of the examination volume, moreover a large amount of computing time must be expended for this calculation.

It is further known that a dose parameter can be calculated based solely on the recording parameters of a computed tomography imaging. This calculation is done specifically only for a particular manufacturer of computed tomography devices or even more specifically for only one type of computed tomography device. This only enables the dose parameter calculated in each case to be compared with restrictions between computed tomography devices of different manufacturers or between different types. Furthermore the dose parameter calculated in each case is not tailored individually to the patient.

The disadvantages of the large volume of data and of the poor comparability become evident above all when pan-device or pan-hospital evaluations of the dose parameter are to be carried out by way of an environment for distributed computing (a Cloud), wherein image data and/or examination data must be stored geographically separated by an evaluation unit and therefore data transmission must take place. A typical problem definition of such an evaluation is comparing the x-ray dose absorbed by the patient for specific computed tomography imaging (of the head for example) with the national average. For this dose parameters for various device types must be calculated from data that is stored in different geographical locations by the evaluation unit. Furthermore the necessary data must also be accessible for the evaluation unit.

SUMMARY

At least one embodiment of the present invention provides a method of calculating the x-ray dose of a computed tomography imaging so that it can be compared independently of the result of the computed tomography imaging, in a rapid manner and without the transmission of large volumes of data.

At least one embodiment is directed to a method for determining a reference dose parameter of a computed tomography imaging; at least one embodiment is directed to a parameter determination unit; at least one embodiment is directed to a computed tomography device; at least one embodiment is directed to a computer program product; and at least one embodiment is directed to a computer-readable storage medium.

Embodiment are described below both in relation to the devices and also in relation to the method. Features, advantages or alternate forms of embodiment mentioned here are likewise also to be transferred to the other embodiments and vice versa. In other words the physical claims (which are directed to a device for example) can also be developed with the claims that are described or claimed in conjunction with a method. The corresponding functional features of embodiments of the method in this case are embodied by corresponding physical modules.

At least one embodiment of the inventive method for determination of a reference dose parameter of a computed tomography imaging is based on a water equivalent diameter (abbreviated to WED) of a slice plane of an examination volume being received via an interface. Furthermore a noise level based on the water equivalent diameter is determined via a computer unit, wherein the noise level is an upper threshold value for the noise of a CT image dataset. Furthermore a reference dose parameter is determined based on the noise level and the water equivalent diameter via the computer unit, wherein the reference dose parameter corresponds to a first x-ray dose that would be absorbed during a recording of a first CT image dataset of the examination volume in the slice plane if the noise of the first CT image dataset corresponds to the noise level, and wherein the reference dose parameter is indirectly proportional to a power of the noise level. In other words, it is not necessary during this determination actually to record the first CT image dataset, the first x-ray dose is only theoretically absorbed in the slice plane, if when using the recording parameter a first CT image dataset examination volume were to be recorded via the computed tomography device.

At least one embodiment of the invention further relates to a parameter determination unit, comprising the following units:

An interface, embodied for first receipt of a water equivalent diameter of a slice plane of an examination volume, A computer unit, embodied for first determination of a noise level based on the water equivalent diameter, wherein the noise level is an upper threshold value for the noise of a CT image dataset, further embodied for second determination of a reference dose parameter based on the noise level and the water equivalent diameter, wherein the reference dose parameter corresponds to a first x-ray dose, which would be absorbed during a recording of a first CT image dataset of the examination volume in the slice plane, if the noise of the first CT image dataset corresponds to the noise level, wherein the reference dose parameter is indirectly proportional to a power of the noise level.

At least one embodiment of the invention further relates to a computed tomography device comprising at least one embodiment of the parameter determination unit. A computed tomography device is embodied in particular to create a tomographic slice image or a three-dimensional image of an examination volume by way of x-ray radiation.

At least one embodiment of the invention also relates to a computer program product with a computer program and also to a computer-readable medium. A largely software-based realization has the advantage that parameter determination units also used previously can be upgraded in a simple manner by a software update, in order to work in the inventive way. Such a computer program product can, as well as the computer program, if necessary comprise additional elements, such as e.g. documentation and/or additional components, as well as hardware components, such as e.g. hardware keys (dongles etc.) for use of the software.

At least one embodiment of the inventive method for determination of a reference dose parameter of a computed tomography imaging, comprises:

receiving, via an interface, a water equivalent diameter of a slice plane of an examination volume;

determining, via a computer unit, a noise level based on the water equivalent diameter, the noise level being an upper threshold value for noise of a CT image dataset;

determining, via the computer unit, a reference dose parameter based on the noise level determined and the water equivalent diameter, the reference dose parameter corresponding to a first x-ray dose, absorbable in the slice plane during a recording of a first CT image dataset of the examination volume upon noise of the first CT image dataset corresponding to the noise level determined.

BRIEF DESCRIPTION OF THE DRAWINGS

The invention will be described and explained in greater detail below with reference to the example embodiments shown in the figures as well as with reference to dummy code.

In the figures

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor;

however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects.

Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for determination of a reference dose parameter of a computed tomography imaging is based on a water equivalent diameter (abbreviated to WED) of a slice plane of an examination volume being received via an interface. Furthermore a noise level based on the water equivalent diameter is determined via a computer unit, wherein the noise level is an upper threshold value for the noise of a CT image dataset. Furthermore a reference dose parameter is determined based on the noise level and the water equivalent diameter via the computer unit, wherein the reference dose parameter corresponds to a first x-ray dose that would be absorbed during a recording of a first CT image dataset of the examination volume in the slice plane if the noise of the first CT image dataset corresponds to the noise level, and wherein the reference dose parameter is indirectly proportional to a power of the noise level. In other words, it is not necessary during this determination actually to record the first CT image dataset, the first x-ray dose is only theoretically absorbed in the slice plane, if when using the recording parameter a first CT image dataset examination volume were to be recorded via the computed tomography device.

The inventor has recognized that the noise level can be determined as an upper threshold value for the noise of a CT image dataset especially efficiently and quickly based on the water equivalent diameter. The inventor has further recognized that both the water equivalent diameter and also the noise level can be used especially efficiently to determine the reference dose parameter, since with the proposed method no large volumes of image data must be transmitted, but also at the same time allowing influences of the nature of the examination region to be included in the determination. In particular the water equivalent diameter of the examination volume (for example of a patient) reflects the physical circumstances of the examination volume in relation to the slice plane, in particular better than in the calculation of the reference dose parameter based on statistical data not related to the respective examination region and/or to the respective patient. The inventor has further recognized that the reference dose parameter, independent of manufacturer of a computed tomography device, is indirectly proportional to a power of the noise level, therefore the reference dose parameter can be determined in particular without using an axial slice image and also independent of manufacturer.

According to a further embodiment of the invention the power has a value of between 0.1 and 2.5, in particular of between 0.5 and 1.5, in particular of between 0.9 and 1.1. In particular the power can have a value of precisely 1. The inventor has recognized that by choosing such a value the reference dose parameter can be determined especially precisely.

According to a further embodiment of the invention the reference dose parameter is further proportional to an exponential function of the water equivalent diameter. The inventor has recognized that the functional dependency of the reference dose parameter on the water equivalent diameter can be described especially well and precisely by an exponential function.

According to a further embodiment of the invention the argument of the exponential function comprises the product of the linear attenuation coefficient of x-ray radiation in water with the water equivalent diameter. The inventor has recognized that the linear attenuation coefficient of water also has an influence on the size of the reference dose parameter, and the common functional dependency of the reference dose parameter on the linear attenuation coefficient and on the water equivalent diameter can be described especially well and precisely by an exponential function of the product of the two variables. Here the argument of a function describes the value from the definition volume of the function, which is used in the function in order to determine the associated function value. Another word for argument of a function is independent variable of the function. The linear attenuation coefficient of x-ray radiation in water is in particular a length, so that the intensity of x-ray radiation falls to a share of $1/e$ ($1/e \approx 0.368$) of the original intensity when the x-ray radiation passes through water on a path with this length, wherein e ($e \approx 2.718$) refers to the Euler number here. In particular the exponential function involves an exponential function for the basis of the Euler number e. 0.19 cm-1 is known in particular as the linear attenuation coefficient of x-ray radiation in water. Absorption coefficient is also known as a synonym for linear attenuation coefficient.

According to a further embodiment of the invention the reference dose parameter is the product of a proportionality constant with the quotient of the exponential function and the power of the noise level, wherein p is the value of the power, wherein the proportionality constant amounts to between 0.2 mGy·HUp and 2, 0 mGy·HUp, or wherein the proportionality constant in particular amounts to between 0.5 mGy·HUp and 1.5 mGy·HUp, or wherein the proportionality constant in particular amounts to between 1.2 mGy·HUp and 1.2 mGy·HUp. Here mGy·HUp refers to the unit Milligray multiplied by Hounsfield unit to the power p. Here the unit one Gray is defined in particular as one Joule per kilogram, and the Hounsfield unit is in particular the unit of the CT number. The inventor has recognized that by the choice of such a proportionality constant the reference dose parameter can be determined especially well and precisely.

According to a further embodiment of the invention, the noise level is a piecewise linear function of the water equivalent diameter. The inventor has recognized that through this functional dependency the noise level can be determined especially well as a function of the water equivalent diameter. A function is in particular piecewise linear when the second derivation of the function at each point is either zero or is not defined.

According to a further embodiment of the invention, the noise level is a constant, sectionally defined function of the water equivalent diameter with precisely two sections, wherein the first section is a constant function and wherein the second section is a linear function of the water equivalent diameter. The inventor has recognized that through this functional dependency the noise level can be determined especially well as a function of the water equivalent diameter. In particular the first section comprises smaller water equivalent diameters than the second section.

The noise level s can be expressed in particular by the formula $s = \max(c, m \cdot WED - t)$, wherein the variables c, m and t are constants. The constant c can be chosen in particular as between 0 HU and 10 HU, in particular as between 2 HU and 6 HU or in particular as between 3 HU and 5 HU, furthermore the constant c can be chosen in particular as 4 HU. The constant m can be chosen in particular as between 0.5 HU/cm and 3 HU/cm, in particular as between 0.5 HU/cm and 2 HU/cm, in particular as between 0.75 HU/cm and 1.25 HU/cm, in particular the constant m can also be chosen as 1.0 HU/cm. The constant t can be chosen as between 0 HU and 30 HU, in particular as between 10 HU and 20 HU, in particular as between 12 HU and 16 HU, but the constant t can also in particular be chosen as 14 HU. The inventor has recognized that by such a choice of one or more of the constants the dependence of the noise levels on the water equivalent diameter can be described especially well.

According to a further embodiment of the invention, a size-specific dose estimation, abbreviated to SSDE, based on the reference dose parameter can further be determined via the computer unit. In particular the size-specific dose estimation is calculated as a product of the reference dose parameter with a function, wherein the function depends on the water equivalent diameter, but not on the reference dose parameter. The function can in particular allocate a correction factor to a water equivalent parameter. The function can in this case in particular be given as a table, wherein the table allocates a plurality of water equivalent diameters to a correction factor in each case, and wherein function values for non-tabulated water equivalent diameters are determined by interpolation, in particular by linear interpolation. The inventor has recognized that the size-specific dose estimation can be calculated especially well and precisely in this way on the basis of the reference dose parameter.

According to a further embodiment of the invention, a recording parameter of a computed tomography device is determined via the computer unit based on the reference dose parameter, wherein a second x-ray dose corresponds to the reference dose parameter, wherein the second x-ray dose would be absorbed during recording of a second CT image dataset in the slice plane if the second CT image dataset is recorded using the recording parameter by way of the computed tomography device. In other words it is not necessary here actually to record the second CT image dataset, the second x-ray dose is only theoretically absorbed in the slice plane if, using the recording parameter, a second CT image dataset would be recorded by way of the computed tomography device. In particular the recording parameter can also furthermore be based on the water equivalent diameter.

Optionally in this embodiment of the invention, the determination of the second CT image dataset can also be recorded subsequently via the computed tomography device. The inventor has recognized that by this method step a recording parameter can be determined especially efficiently and easily, so that the second x-ray dose lies as close as possible to the reference dose parameter, and thus the patient is subjected to an x-ray dose that is as small as possible. In particular in this way the recording parameters can be determined before the actual examination. A recording parameter can for example involve the x-ray voltage of the x-ray tubes, or the x-ray current of the x-ray tubes, or the slice thickness of the second CT image dataset, or the pitch factor of a spiral recording, or further known parameters of computed tomography.

According to a further possible embodiment of the invention, a planning examination volume is furthermore received via the interface. The planning examination volume can in particular describe the examination volume to be recorded during the first CT image dataset. Furthermore, based on the reference dose parameter, a planning dose parameter can be calculated via the computer unit, wherein an x-ray dose absorbed in the planning examination volume corresponds to the planning dose parameter, if a CT image dataset of the planning examination volume is recorded, wherein the noise of the CT image dataset of the planning examination volume corresponds to the noise level. Furthermore the planning dose parameter can be displayed. The planning dose parameter can in particular involve a dose length product. The inventor has recognized that, based on the planning dose parameter, there can be an especially effective and precise planning of a computed tomography examination.

According to a further embodiment of the invention, a real dose parameter of a recording of a third CT image dataset of the examination volume is furthermore received via the interface. Furthermore, based on a comparison of the reference dose parameter and the real dose parameter, the power and/or the proportionality constant is corrected via the computer unit. The inventor has recognized that through the correction based on such a comparison, the proportionality constant can be corrected especially quickly and simply. This can be used in particular to determine or to optimize the proportionality constant for various computed tomography products, in particular for various computed tomography products of different manufacturers.

At least one embodiment of the invention further relates to a parameter determination unit, comprising the following units:

An interface, embodied for first receipt of a water equivalent diameter of a slice plane of an examination volume, A computer unit, embodied for first determination of a noise level based on the water equivalent diameter, wherein the noise level is an upper threshold value for the noise of a CT image dataset, further embodied for second determination of a reference dose parameter based on the noise level and the water equivalent diameter, wherein the reference dose parameter corresponds to a first x-ray dose, which would be absorbed during a recording of a first CT image dataset of the examination volume in the slice plane, if the noise of the first CT image dataset corresponds to the noise level, wherein the reference dose parameter is indirectly proportional to a power of the noise level.

Such a parameter determination unit can be embodied in particular to carry out embodiments of the inventive method described above. The parameter determination unit is embodied to carry out this method and its embodiments, in that the interface and the computer unit are embodied to carry out the corresponding method steps.

At least one embodiment of the invention further relates to a computed tomography device comprising at least one embodiment of the parameter determination unit. A computed tomography device is embodied in particular to create a tomographic slice image or a three-dimensional image of an examination volume by way of x-ray radiation.

At least one embodiment of the invention also relates to a computer program product with a computer program and also to a computer-readable medium. A largely software-based realization has the advantage that parameter determination units also used previously can be upgraded in a simple manner by a software update, in order to work in the inventive way. Such a computer program product can, as well as the computer program, if necessary comprise additional elements, such as e.g. documentation and/or additional components, as well as hardware components, such as e.g. hardware keys (dongles etc.) for use of the software.

A water equivalent diameter of a patient describes the overall attenuation of x-ray radiation by the patient standardized to the attenuation of water. A water equivalent diameter of a patient can be defined in particular as the diameter of a water cylinder, wherein the water cylinder, during computed a tomography imaging causes the same overall attenuation of the x-ray intensity as the patient, if the slice plane of the axial slice images is arranged orthogonally to the axis of symmetry of the water cylinder. The water equivalent diameter can also be direction-dependent, in particular since the cross-section of a patient is not generally circular in shape. One method for calculating the water equivalent diameter on the basis of an axial slice image is known for example from the publication American Association of Physicists in Medicine (2014): "Use of Water Equivalent Diameter for Calculating patient Size and Size-Specific Dose Estimates (SSDE) in CT (Task Group 220)", the entire contents of which are hereby incorporated herein by reference. Furthermore the water equivalent diameter can also be calculated on the basis of a topogram, for example by a threshold value segmentation along a straight line.

A reference dose parameter and/or a real dose parameter can correspond in particular to a computed tomography dose index, abbreviated to CTDI, in particular to a weighted computed tomography dose index, abbreviated to CTDIw, in particular to the volume-related computed tomography dose index, abbreviated to CTDIvol, of a spiral computed tomography.

The computed tomography dose index (abbreviated to CTDI) can be defined via the formula $$CTDI = \frac{1}{nT}\int_{-7T}^{7T} D(z)dz,$$

wherein T is the slice thickness of the computed tomography recording, n is the number of slices and D(z) is the dose measured at a location z by way of dosimeter in a phantom. Usually a phantom with diameter 16 cm or with diameter 32 cm is used here. Usually the measurement is carried out with a 100 mm long pin chamber dosimeter, and the definition of the CTDI is modified as $$CTDI_{100} = \frac{1}{nT}\int_{-50\,mm}^{50\,mm} D(z)dz.$$

Since the dose in the patient close to the surface is higher than it is inside the patient, the weighted $CTDI_w$ is used $$CTDI_w = \tfrac{1}{3}CTDI_{100}^{central} + \tfrac{2}{3}CTDI_{100}^{peripher},$$

wherein $CTDI_{100}^{central}$ is measured in the middle of the phantom, and $CTDI_{100}^{peripher}$ is measured at the periphery of the phantom.

In many computed tomography devices it is possible to carry out a spiral scan. Here the examination volume is moved at a constant speed through the computed tomography device, while the x-ray source is rotated with a constant angular velocity within the computed tomography device. The x-ray source therefore moves relative to the examination volume on a spiral, in particular on a helix. A spiral scan is described by the pitch factor p, which is defined as P=d/(M·T), wherein d refers to the distance covered by the examination volume during a complete orbit of the x-ray source, and wherein M is the number of rows of the x-ray detector used, and wherein T is the slice thickness. The pitch factor can in particular assume values between 0 and 2. $CTDI_{vol}$ is used as a measure for the dose for a spiral scan, which is the $CTDI_w$ corrected by the pitch factor, according to the following formula $$CTDI_{vol} = \frac{CTDI_w}{P}.$$

A reference dose parameter and/or a real dose parameter can also correspond to the dose length product, abbreviated to DLP. Here the dose length product is defined in particular as the product of a computed tomography dose index with the axial length of the examination volume.

As well as the computed tomography dose index and the dose length product, the size-specific dose estimation, abbreviated to SSDE, is also known. This is based on the computed tomography dose index of a computed tomography imaging and additionally relates to a water equivalent diameter of a patient. For definition of the various dose parameters the reader is also referred in particular to the publication American Association of Physicists in Medicine (2008): "The Measurement, Reporting, and Management of Radiation Dose in CT (Task Group 23)", the entire contents of which are hereby incorporated herein by reference.

A topogram is in particular a two-dimensional overview recording of the examination volume by way of x-ray radiation, it can in particular correspond to a two-dimensional x-ray recording, in particular to a fluoroscopy recording. For recording of a topogram an examination volume can be moved past the cone beam of the stationary tubes with the aid of a movable table. A topogram can in particular involve an x-ray projection relating to a projection direction. A topogram can in particular be a lateral topogram or an anterior-posterior topogram.

Figure 1:
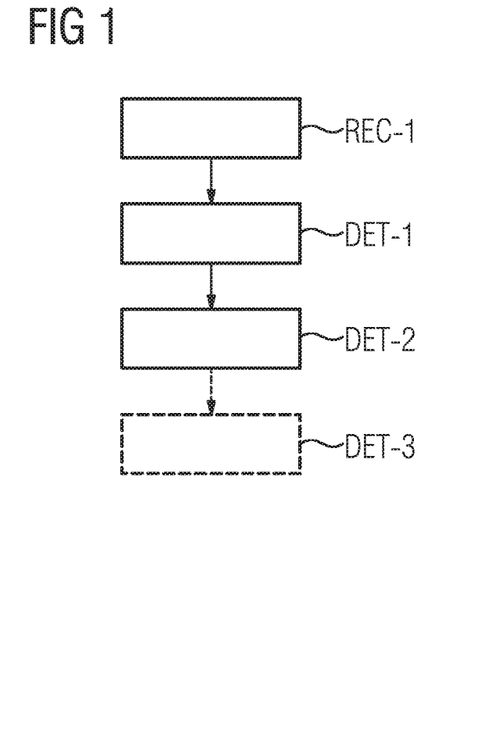
FIG. 1 shows a flow diagram of a first example embodiment for determination of a reference dose parameter.

FIG. 1 shows a flow diagram of a first example embodiment for determination of a reference dose parameter.

The first step of the first example embodiment shown is the first receipt REC-1 of a water equivalent diameter of a slice plane of an examination volume via an interface 401. The water equivalent diameter can in particular have been recorded beforehand based on a topogram of the examination volume.

The second step of the first example embodiment shown is the first determination DET-1 of a noise level based on the water equivalent diameter via a computer unit 402, wherein the noise level is an upper threshold value for the noise of a CT image dataset. In this example embodiment the noise of a CT image is defined as the standard deviation of the measured Hounsfield units of a region, which has constant real Hounsfield units. This region with constant real Hounsfield units can involve the air shown in the image dataset, as an alternative the noise can also always be determined by computed tomography imaging of an at least partly homogeneous phantom. In the example embodiment shown the noise level s is determined by the formula $$s = \max(c, m \cdot WED + t)$$

wherein the constants are selected here as c=4 HU, m=1 HU/cm and t=−14 HU. It is naturally also possible to choose different constants, in order to comply with changed requirements for the calculation. Furthermore max(a,b) refers here to the maximum of a variable a and a variable b, in other words max(a,b)=a, if a is greater than or equal to b, and max(a,b)=b, if b is greater than a.

The next step of the first example embodiment shown is the second determination DET-2 of a reference dose parameter based on the noise level and the water equivalent diameter via the computer unit 402, wherein the reference dose parameter corresponds to a first x-ray dose, which would be absorbed in the slice plane during a recording of a first CT image dataset of the examination volume, if the noise of the first CT image dataset corresponds to the noise level.

Further, in at least one embodiment, the reference dose parameter is indirectly proportional to a power of the noise level. The reference dose parameter in this example embodiment is a computed tomography dose index, abbreviated to CTDI, in particular the CTDIvol of a spiral scan.

In the example embodiment shown the reference dose parameter is calculated as $$CTDI_{vol}(WED, s) = k \cdot \frac{\exp(l_w \cdot WED)}{s},$$

wherein here the value p of the power is precisely 1, wherein k is a proportionality constant, which in this example embodiment is chosen as k=1 mGy·HU, and $l_w$ is the linear attenuation coefficient of x-ray radiation in water. Here $l_w=0.19$ cm$^{-1}$ is usually assumed as the linear attenuation coefficient. As an alternative the reference dose parameter can also be calculated as $$CTDI_{vol}(WED, s) = k \cdot \exp(l_w \cdot WED) \cdot \left(\frac{s_0}{s}\right)^p,$$

wherein $s_0$ is a scaling factor of the noise level, wherein the unit of the scaling factor of the noise level is likewise an HU or Hounsfield unit. In this case the proportionality constant k bears the unit mGy. If with this alternate calculation method $s_0=1$ HU and $p=1$ is chosen, both methods of calculation are identical.

The next step of the example embodiment shown is the third determination DET-3 of a size-specific dose estimation based on the reference dose parameter via the computer unit 402. This involves an optional step, which does not have to be implemented in each example embodiment of the inventive method.

The size-specific dose estimation is calculated in this example embodiment as

SSDE(WED,s)=f(WED)·CTDI$_{vol}$(WED,s), wherein f is a function, which depends only on the water equivalent diameter WED, but not on CTDI$_{vol}$. The function f is given in this example embodiment by a table, which comprises the function values for a number of values of the water equivalent diameter. These function values are often also referred to as correction factors. A function value for a non-tabulated water equivalent diameter can be determined by interpolation, in particular by linear interpolation of two or more function values of tabulated water equivalent diameters.

This example embodiment can be used, during computed tomography imaging, to compare the real dose parameter, here in particular the CTDIvol, given by the real imaging, with the reference dose parameter, here the CTDIvol calculated based on the water equivalent diameter, and in this way to assess the imaging in respect of the dose absorbed by the patient. This assessment can in particular be undertaken without calling up or analyzing the axial image data recorded during computed tomography imaging. Therefore this example embodiment in particular is also suitable for assessing a large number of computed tomography imagings, wherein the data of the computed tomography imagings is stored geographically separated from the evaluation unit. As an alternative the assessment can also be carried out in relation to the size-specific dose estimation in each case.

TABLE A

| Dummy code for the first example embodiment | |
|---|---|
| A.1 | function noise(WED): |
| A.2 | m = 1.0; t = −14.0; c = 4.0 |
| A.3 | return max(c, m*WED + t) |
| A.4 | function ctdi_vol(WED): |
| A.5 | k = 1.0; l_water = 0.19 |
| A.6 | return k*exp(l_water * WED) / noise(WED) |
| A.7 | function ssde(WED, cor_factors): |
| A.8 | WED_1 = lower_key(cor_factors, WED) |
| A.9 | WED_2 = upper_key(cor_factors, WED) |
| A.10 | cor_factor = (cor_factors[WED_2] − cor_factors[WED_1]) * (WED − WED_1)/(WED_2 − WED_1) + cor_factors[WED_1] |
| A.11 | return cor_factor*WED |

Table A shows dummy code for the first example embodiment. Listed in code lines A.1. A.4 and A.7 are the function declarations for determining the noise level, the CTDI$_A$ and the SSDE. Chosen in code lines A.2 and A.5 are the constant parameters as described for the first example embodiment. The code lines A.3 and A.6 correspond to the already described formulae for determining the noise level and the CTDI$_{vol}$. The function ssde, as well as the water equivalent diameter, also has a list cor_factors with pairs of water equivalent diameters and associated correction factors passed to it. The function lower_key in the code line A.8 enables the largest water equivalent diameter of the cor_factors to be determined, which is still smaller than the water equivalent diameter passed to the function. The function upper_key in the code line A.9 enables the smallest water equivalent diameter of the list cor_factors to be determined, which is still larger than the water equivalent diameter passed to the function. At this point a further interrogation can optionally be built in as to whether the water equivalent diameter passed to the function is contained in the list cor_factors, and the assigned correction factor multiplied by the water equivalent diameter passed to the function can be returned. If the interrogation is negative, or in the listed dummy code of Table A in the code line A.10 a linear interpolation of the correction factor cor_factor is always calculated, which is multiplied in code line A.11 by the water equivalent diameter passed to the function.

Figure 2:
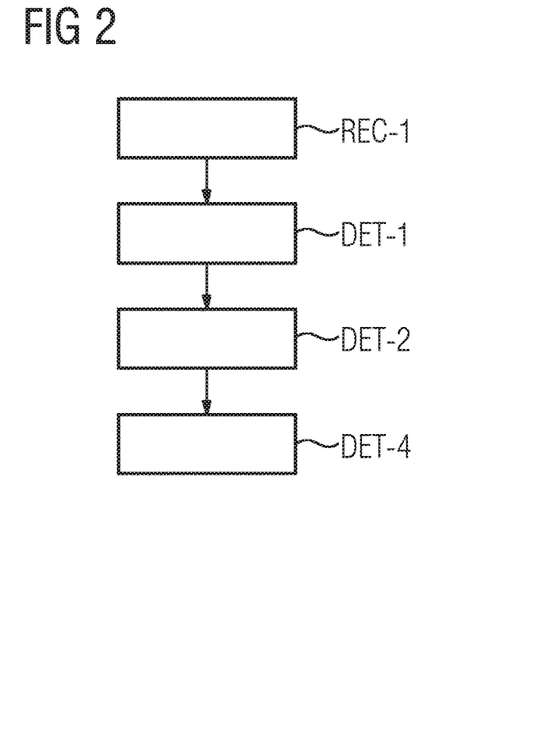
FIG. 2 shows a flow diagram of a second example embodiment for determination of a reference dose parameter.

FIG. 2 shows a flow diagram of a second example embodiment for determination of a reference dose parameter. The method steps of first receipt REC-1, of first determination DET-2 and of second determination DET-3 are carried out analogously to the description of the first example embodiment.

A further step of the second example embodiment shown is the fourth determination DET-4 of a recording parameter of a computed tomography device 420 based on the reference dose parameter via the computer unit 402, wherein a second x-ray dose corresponds to the reference dose parameter, wherein the second x-ray dose would be absorbed in the slice plane during recording of a second CT image dataset if the second CT image dataset is recorded using the recording parameter via the computed tomography device 420. In the example embodiment shown the recording parameter is the x-ray current of the x-ray tubes of the computed tomography device 420. If the computed tomography device 420 comprises means for dose modulation, in particular by variation of the x-ray current, then the recording parameter can alternately also be an average value of the x-ray current of the x-ray tubes of the computed tomography device 420.

If the x-ray current as well as all further variables influencing the computed tomography (such as for example pitch factor or x-ray voltage) are predetermined, it is possible to determine the CTDI$_{vol}$ of an imaging using the x-ray current and the further variables. For example the CTDI$_{vol}$ can be calculated on the basis of tabulated measurement values, wherein the measurement values are recorded by way of one or more dosimeters in a phantom. If, for a specific combination of x-ray current and the further variables, no measurement values are tabulated, then these can be interpolated, in particular interpolated linearly. Thus in particular, if the other variables are kept constant, a function can be determined, which describes the CTDI$_{vol}$ as a function of the x-ray current.

Since the x-ray dose absorbed in the examination volume is directly proportional to the x-ray current, the CTDI$_{vol}$ also increases monotonously with the x-ray current. It is therefore possible to determine the x-ray current so that the CTDI$_{vol}$ corresponds to the reference dose parameter, in that the reciprocal function is determined, which describes the x-ray current as a function of the $CTDI_{vol}$. The determination of the reciprocal function can in particular also be carried out graphically or numerically, so that it is not necessary to know the original function term.

TABLE B

Dummy code for the third example embodiment

| | |
|---|---|
| B.1 | function xray_current_it(ctdi_vol, imaging_params, current_lower, current_upper): |
| B.2 | ctdi_vol_calc_lower = scanner.ctdi_vol(imaging_params, current_lower) |
| B.3 | ctdi_vol_calc_upper = scanner.ctdi_vol(imaging_params, current_upper) |
| B.4 | current_mid = (current_lower + current_upper)/2 |
| B.5 | ctdi_vol_calc_mid = scanner.ctdi_vol(xray_current, current_mid) |
| B.6 | if abs(ctdi_vol_calc_mid − ctdi_vol)/ ctdi_vol < 0.01: |
| B.7 | return current_mid |
| B.8 | else if ctdi_vol_calc_mid > ctdi_vol: |
| B.9 | return xray_current_it(ctdi_vol, imaging_params, current_lower, current_mid) |
| B.10 | else: |
| B.11 | return xray_current_it(ctdi_vol, imaging_params, current_mid, current_upper) |
| B.12 | function xray_current(WED, imaging_params): |
| B.13 | ctdi_vol_ref = ctdi_vol(WED) |
| B.14 | current_max = scanner.xray_current_max |
| B.15 | return xray_current_it(ctdi_vol_ref, imaging_params, 0. current_max) |

Table B shows dummy code for the second example embodiment. Defined in the code lines B.1, . . . , B.11 is a function for iterative determination of the x-ray current, which is based on the bisection method. Defined in the code lines B.12, . . . , B.15 is a function for determining the x-ray current based on the water equivalent diameter WED and the further variables imaging_params.

In code line B.13 the reference $CTDI_{vol}$ is calculated by way of the function defined in Table A. Called in code line B.14 is the maximum x-ray current current_max of the scanner. Code line B.15 calls the iterative function for determining the x-ray current.

Calculated in code lines B.2 and B.3 by way of a function made available by the scanner is the $CTDI_{vol}$, wherein two different x-ray currents current_lower and current_upper are used, so that the $CTDI_{vol}$ in the first case is smaller than the reference $CTDI_{vol}$ and in the second case is larger than the reference $CTDI_{vol}$. The function made available by the scanner for calculating the $CTDI_{vol}$ calculates these dose parameters as a function of the given recording parameters.

Determined in code line B.4 is a further x-ray current current_mid as the mid value of the x-ray currents current_lower and current_upper, furthermore in code line B.5 the $CTDI_{vol}$ for this x-ray current is determined.

If the $CTDI_{vol}$ for the mid value of the x-ray currents current_lower and current_upper is close enough to the reference $CTDI_{vol}$ (in the dummy code shown here, when the relative deviation is less than 1 percent), this mid value of the x-ray current is returned in code line B.6 and B.7. Otherwise the function is called iteratively in code lines B.8, . . . , B.11, wherein the function parameters of the x-ray currents are determined based on the $CTDI_{vol}$ at the mid value of the x-ray current.

Figure 3:
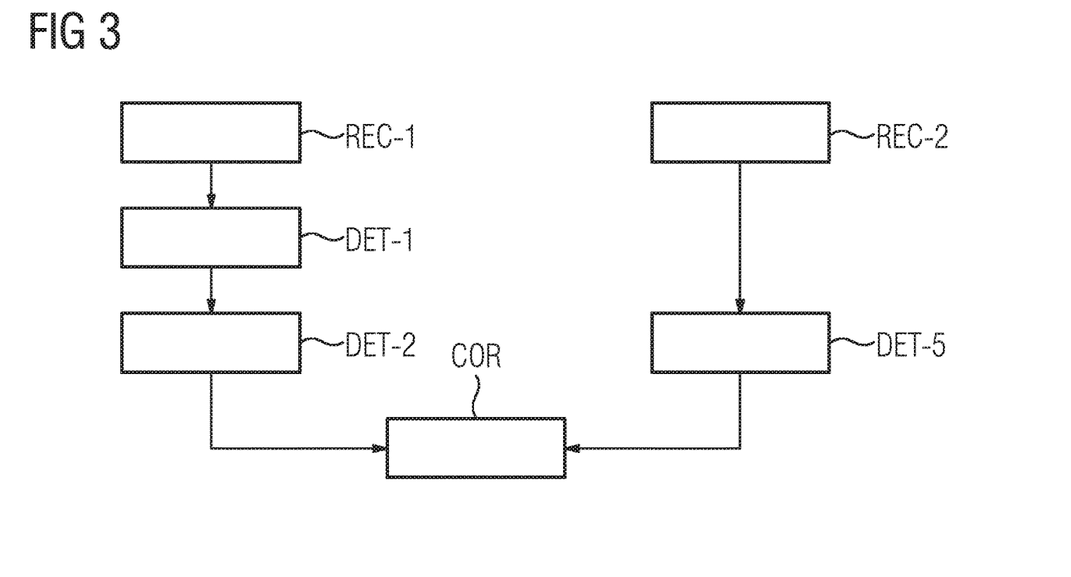
FIG. 3 shows a flow diagram of a third example embodiment for determination of a reference dose parameter.

FIG. 3 shows a flow diagram of a third example embodiment for determination of a reference dose parameter. The method steps of first receipt REC-1, first determination DET-2 and of second determination DET-3 are carried out analogously to the description of the first example embodiment.

Furthermore in the third example embodiment there is a second receipt REC-2 of a real dose parameter of a recording of a third CT image dataset of the examination volume via the interface 401. wherein the real dose parameter corresponds to the third x-ray dose absorbed in the slice plane during the recording of the third CT image dataset. Furthermore in the second receipt REC-2 the noise level of the third CT image dataset is also received.

Furthermore in the third example embodiment there is a correction COR of the power and/or the proportionality constant based on a comparison of the reference dose parameter and the real dose parameter via the computer unit 402. A correction can in particular be realized by adaptation of the function equation, in which the power and/or the proportionality constant are entered as fit parameters. The adaptation of a function equation can be carried out in particular by way of the Levenberg-Marquardt algorithm. The function equation can in particular be given by the function $CTDI_{vol}(WED, s)$ defined in the information for the first example embodiment. Further pairs of reference dose parameters and real dose parameters can in particular also be included in the adaptation of the function equation.

The third example embodiment shown is advantageous in particular if the power and/or the proportionality constant have to be chosen separately for various computed tomography devices or different manufacturers in each case.

Figure 4:
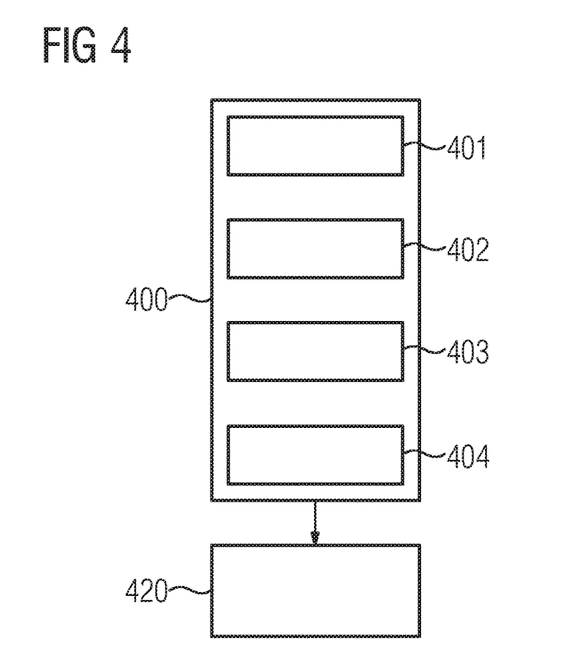
FIG. 4 shows a parameter determination unit.

FIG. 4 shows a parameter determination unit 400 for determining a reference dose parameter. The parameter determination unit 400 shown here is designed to carry out an embodiment of the inventive method. This parameter determination unit 400 comprises an interface 401, a computer unit 402, a memory unit 403 and also an input and output unit 404.

The parameter determination unit 400 can in particular involve a computer, a microcontroller or an integrated circuit. As an alternative the parameter determination unit 400 can involve a real or virtual network of computers (a real network is known as a cluster, a virtual network is known as a Cloud).

An interface 401 can involve a hardware or software interface (for example PCI bus, USB or Firewire). A computer unit 402 can have hardware elements or software elements, for example a microprocessor or a so-called FPGA (Field Programmable Gate Array). A memory unit 403 can be realized as Random Access Memory (RAM) or as permanent mass storage (hard disk, USB stick, SD card, solid state disk). An input and output unit 404 comprises at least one input unit and/or at least one output unit.

Figure 5:
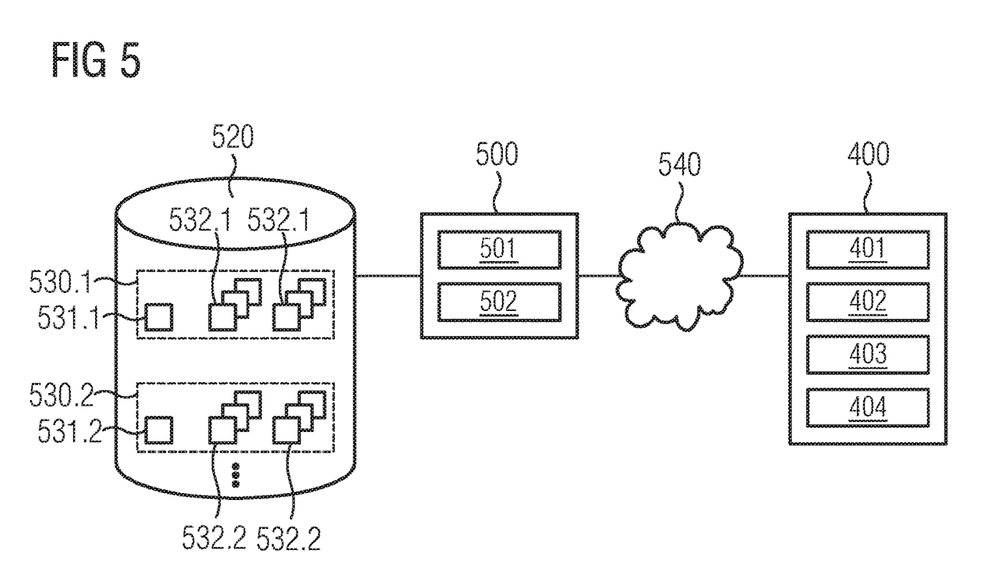
FIG. 5 shows a parameter determination unit in an environment for distributed computing.

FIG. 5 shows an example embodiment of a possible incorporation of a parameter determination unit 400 into an environment for distributed computing. The parameter determination unit is connected via a network 540 to a server 500, which for its part is connected to a database 520.

A server 500 can in particular involve a computer, a microcontroller or an integrated circuit. As an alternative the server 500 can involve a real or virtual network of computers (a real network is known as a cluster, a virtual network is known as a Cloud).

The server comprises a server interface 501 and a server computer unit 502. A server interface 501 can involve a hardware or software interface (for example PCI bus, USB or Firewire). A server computer unit 502 can have hardware elements or software elements, for example a microprocessor or a so-called FPGA (Field Programmable Gate Array).

The database 520 can be realized in a memory of the server 500, but it can also be embodied, as in the example embodiment shown, as a separate database server. The database 520 comprises a plurality of examination datasets 530.1. 530.2, each of the examination datasets 530.1. 520.2 comprises a topogram recording 531.1. 531.2 of an examination region and also one or more image series 532.1. 532.2 comprising axial slice images of the examination region.

A network 540 can involve a local area network, abbreviated to LAN, or a wide area network, abbreviated to WAN. An example for a LAN is an intranet, an example for a WAN is the Internet. The connection is such cases can be made via cables (for example via Ethernet, PowerLAN or Token-Ring), as an alternative the connection can also be wireless (for example via a wireless local area network, abbreviated to WLAN, or infrared or Bluetooth). In the example embodiment shown the network 540 corresponds to the Internet.

In the example embodiment shown the server 500 and the database 520 are part of an architecture for distributed computing. The database 520 stores data from a large number of computed tomography imagings, the server 500 regulates the access to the database 520. As in the first example embodiment, the reference value of the CTDIvol and/or of the SSDE is to be calculated from the plurality of computed tomography imagings.

It is known from the prior art that the series of images 532.1. 532.2 of the examination datasets 530.1. 530.2 can be transmitted via the network 540 to the parameter determination unit, in order to calculate from the series of images 532.1. 532.2 comprising axial slice images the respective CTDIvol and/or the SSDE. The calculation on the basis of the axial slice images is slow however, also high volumes of data must be transmitted via the restricted bandwidth of the network 540.

In the example embodiment of the present invention shown only at least one topogram recording 531.1. 531.2 is transmitted via the network 540 to the parameter determination unit 400, but no series of images 532.1. 532.2 comprising axial slice images however. From a topogram recording 531.1. 531.2 a water equivalent parameter of a slice plane can be determined, in that the topogram recording 531.1. 531.2 is compared to reference topogram recordings, for which in each case the water equivalent diameter is known, or by way of a threshold value segmentation. Using the flow diagram shown in FIG. 1, the optimum CTDIvol of the respective recording can then be calculated, and this reference dose parameter can be used for statistics over many computed tomography imagings.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a reference dose parameter of computed tomography (CT) imaging, comprising:
   determining, via a computer unit, a water equivalent diameter of a slice plane of the examination volume based on a topogram of an examination volume of a patient;
   determining, via a computer unit, a noise level based on the water equivalent diameter, the noise level being an upper threshold value for noise of a CT image dataset;
   determining based on the noise level determined and the water equivalent diameter determined, via the computer unit, a reference dose parameter, corresponding to a first x-ray dose, absorbable in the slice plane during a recording of a first CT image dataset of the examination volume, upon noise of the first CT image dataset corresponding to the noise level determined; and
   comparing the reference dose parameter determined, with an actual dose parameter of a real computed tomography examination of the examination volume, to assess or rate quality of the real computed tomography examination.

2. The method of claim 1, wherein the reference dose parameter corresponds to at least one of a computed tomography dose index, a weighted computed tomography dose index, a volume-related computed tomography dose index, and a dose-length product.

3. The method of claim 1, wherein the reference dose parameter is further proportional to an exponential function of the water equivalent diameter.

4. The method of claim 3, wherein an argument of the exponential function includes a product of a linear attenuation coefficient of x-ray radiation in water with the water equivalent diameter.

5. The method of claim 4, further comprising:
   receiving, via the interface, a real dose parameter of a recording of a third CT image dataset of the examination volume, wherein the real dose parameter corresponds to a third x-ray dose absorbed in the slice plane during the recording of the third CT image dataset; and
   correcting at least one of the power and the proportionality constant based on a comparison, via the computer unit, of the reference dose parameter and the real dose parameter.

6. The method of claim 1, wherein the noise level is a piecewise linear function of the water equivalent diameter.

7. The method of claim 1, wherein the noise level is a continuous sectionally-defined function of the water equivalent diameter with a first section and a second section, wherein the first section is a constant function and wherein the second section is a linear function of the water equivalent diameter.

8. The method of claim 1, further comprising:
determining, via the computer unit, a size-specific dose estimation based on the reference dose parameter, for adjustment of x ray radiation of an x ray tube of a computed tomography device used in the CT imaging.

9. The method of claim 1, further comprising:
determining, via the computer unit, a recording parameter of a computed tomography device based on the reference dose parameter, wherein a second x-ray dose corresponds to the reference dose parameter, and wherein the second x-ray dose is absorbable in the slice plane during recording of a second CT image dataset upon the second CT image dataset being recorded using the recording parameter.

10. The method of claim 1, wherein the reference dose parameter is usable to determine a size-specific dose estimation, for subsequent adjustment of x-ray radiation of an x-ray tube of a computed tomography device used in the CT imaging.

11. A non-transitory computer program product including a computer program, directly loadable into a memory of a parameter determination unit, including program sections to carry out the method of claim 1 when the program sections are executed by the parameter determination unit.

12. A non-transitory computer-readable storage medium, storing program sections readable and executable by a parameter determination unit, to carry out the method of claim 1 when the program sections are executed by the parameter determination unit.

13. A parameter determination unit comprising:
an interface, embodied to receive a topogram of an examination volume; and
a computer unit, embodied to
determine a water equivalent diameter of a slice plane of the examination volume based upon the topogram,
determine a noise level based on the water equivalent diameter, the noise level being an upper threshold value for noise of a CT image dataset, and
determine a reference dose parameter corresponding to a first x-ray dose, absorbable in a slice plane during a recording of a first CT image dataset of the examination volume upon noise of the first CT image dataset corresponding to the noise level determined, wherein the computer unit is further embodied to compare the reference dose parameter determined, with an actual dose parameter of a real computed tomography examination of the examination volume, to assess or rate quality of the real computed tomography examination.

14. The parameter determination unit of claim 13, wherein the computer unit is further embodied to determine a size-specific dose estimation, based upon the reference dose parameter, for subsequent adjustment of x-ray radiation of an x-ray tube of a computed tomography device used in the CT imaging.

15. The parameter determination unit of claim 13, wherein the computer unit is further embodied to determine, a recording parameter of a computed tomography device, based on the reference dose parameter, wherein a second x-ray dose corresponds to the reference dose parameter, and wherein the second x-ray dose is absorbable in the slice plane during recording of a second CT image dataset upon the second CT image dataset being recorded using the recording parameter.

16. A computed tomography device comprising:
the parameter determination unit of claim 13.

17. The parameter determination unit of claim 13, wherein the reference dose parameter corresponds to at least one of a computed tomography dose index, a weighted computed tomography dose index, a volume-related computed tomography dose index, and a dose-length product.

18. A method for determining a reference dose parameter of computed tomography (CT) imaging, comprising:
determining, via at least one processor, a water equivalent diameter of a slice plane of an examination volume based on a topogram of the examination volume of a patient;
determining, via at least one processor, a noise level based on the water equivalent diameter, the noise level being an upper threshold value for noise of a CT image dataset; and
determining based on the noise level determined and the water equivalent diameter determined, via the at least one processor, a reference dose parameter, corresponding to a first x-ray dose, absorbable in the slice plane during a recording of a first CT image dataset of the examination volume, upon noise of the first CT image dataset corresponding to the noise level determined, wherein the reference dose parameter is usable to determine a size-specific dose estimation, for subsequent adjustment of x-ray radiation of an x-ray tube of a computed tomography device used in the CT imaging.

19. A non-transitory computer-readable storage medium, storing program sections readable and executable by a parameter determination unit, to carry out the method of claim 18 when the program sections are executed by the parameter determination unit.

20. A parameter determination unit comprising:
at least one processor, embodied to
determine a water equivalent diameter of a slice plane of an examination volume based on a topogram of the examination volume of a patient;
determine a noise level based on the water equivalent diameter, the noise level being an upper threshold value for noise of a CT image dataset, and
determine based on the noise level determined and the water equivalent diameter determined, a reference dose parameter, corresponding to a first x-ray dose, absorbable in a slice plane during a recording of a first CT image dataset of the examination volume, upon noise of the first CT image dataset corresponding to the noise level determined, wherein the at least one processor is further embodied to determine a size-specific dose estimation, for subsequent adjustment of x-ray radiation of an x-ray tube of a computed tomography device used in the CT imaging.

* * * * *